(12) United States Patent
Maximos

(10) Patent No.: US 11,357,395 B2
(45) Date of Patent: Jun. 14, 2022

(54) TRACHEOSCOPE CONTROL DEVICE, LARYNGEAL MASK AIRWAY DEVICE, AND COMBINATION SYSTEM THEREOF

(71) Applicant: Robert B Maximos, Washington, DC (US)

(72) Inventor: Robert B Maximos, Washington, DC (US)

(*) Notice: Subject to any disclaimer, the term of this patent is extended or adjusted under 35 U.S.C. 154(b) by 213 days.

(21) Appl. No.: 16/458,674

(22) Filed: Jul. 1, 2019

(65) Prior Publication Data
US 2021/0000336 A1    Jan. 7, 2021

(51) Int. Cl.
| | |
|---|---|
| A61B 1/267 | (2006.01) |
| A61B 1/005 | (2006.01) |
| A61B 1/008 | (2006.01) |
| A61B 1/00 | (2006.01) |
| A61B 1/04 | (2006.01) |
| A61B 1/015 | (2006.01) |
| A61M 16/04 | (2006.01) |
| A61B 1/05 | (2006.01) |
| A61M 25/01 | (2006.01) |

(52) U.S. Cl.
CPC .............. *A61B 1/267* (2013.01); *A61B 1/008* (2013.01); *A61B 1/00009* (2013.01); *A61B 1/00045* (2013.01); *A61B 1/0052* (2013.01); *A61B 1/0055* (2013.01); *A61B 1/0057* (2013.01); *A61B 1/00128* (2013.01); *A61B 1/015* (2013.01); *A61B 1/042* (2013.01); *A61B 1/051* (2013.01); *A61M 16/0447* (2014.02); *A61M 16/0488* (2013.01); *A61M 25/0147* (2013.01)

(58) Field of Classification Search
CPC ............................ A61B 1/0051; A61B 1/0052
See application file for complete search history.

(56) References Cited

U.S. PATENT DOCUMENTS

| | | | | |
|---|---|---|---|---|
| 5,569,157 | A * | 10/1996 | Nakazawa ........... | A61B 1/0008 600/104 |
| 10,112,024 | B2* | 10/2018 | Geraghty ............ | A61M 16/085 |
| 10,561,822 | B2* | 2/2020 | Wang ................... | A61B 1/0057 |
| 2006/0162730 | A1 | 7/2006 | Glassenberg et al. | |
| 2006/0180155 | A1 | 8/2006 | Glassenberg et al. | |
| 2007/0175482 | A1 | 8/2007 | Kimmel et al. | |
| 2007/0198000 | A1* | 8/2007 | Miyamoto ......... | A61B 1/00154 604/523 |
| 2009/0209820 | A1* | 8/2009 | Tanaka ............... | A61M 25/0147 600/149 |
| 2009/0247828 | A1* | 10/2009 | Watanabe .......... | A61B 1/00039 600/131 |
| 2011/0295242 | A1* | 12/2011 | Spivey ........... | A61B 17/320016 606/1 |
| 2011/0315147 | A1* | 12/2011 | Wood .................. | A61M 16/042 128/207.15 |

(Continued)

*Primary Examiner* — Michael J Carey
*Assistant Examiner* — Minqiao Huang

(57) ABSTRACT

An articulating tracheoscope control device, a laryngeal mask airway (LMA) device, and an articulating tracheoscope control device and LMA device combination system, that can control precise movement of a distal end of a tracheoscope with a patient's larynx within an angular range of at least 180 degrees and can lock the distal end of the tracheoscope in any desired position within the patient's larynx such that managing the tracheoscope during a tracheostomy procedure is not required in order to monitor the tracheostomy procedure.

8 Claims, 11 Drawing Sheets

(56) References Cited

U.S. PATENT DOCUMENTS

| | | | |
|---|---|---|---|
| 2013/0012929 A1* | 1/2013 | Malkowski | A61B 1/0052 606/1 |
| 2016/0256648 A1 | 9/2016 | Molnar | |
| 2017/0325659 A1* | 11/2017 | Wang | A61B 1/0052 |
| 2018/0085545 A1* | 3/2018 | Maslow | A61B 1/2673 |
| 2018/0206706 A1* | 7/2018 | Wang | A61B 1/005 |
| 2018/0207403 A1* | 7/2018 | Wang | A61M 25/01 |

* cited by examiner

TRACHEOSCOPE CONTROL DEVICE, LARYNGEAL MASK AIRWAY DEVICE, AND COMBINATION SYSTEM THEREOF

BACKGROUND OF THE INVENTIVE CONCEPT

1. Field of the Invention

The present inventive concept relates to a tracheoscope control device, a laryngeal mask airway (LMA) device, and a combination system thereof that can control a distal end of a tracheoscope while disposed in the larynx of a patient. More particularly, the present inventive concept relates to a tracheoscope control device, a laryngeal mask airway device, and a combination system thereof that can articulate a camera disposed at a distal end of a tracheoscope by an angular range of at least 180 degrees and can lock the camera head at any desired angle while disposed at a patient's tracheal tube.

2. Description of the Related Art

Tracheoscopy is a nonsurgical procedure used to examine the interior of a patient's trachea. A laryngeal mask airway (LMA) device, also known as a laryngeal mask, is a medical device that keeps a patient's airway open when a patient is under anesthesia or unconsciousness. It is then used as a conduit for providing oxygen and other gases to the patient, thereby maintaining ventilation and oxygenation. An LMA is generally composed of an airway tube that is connected to an elliptical mask with a surrounding cuff which is inserted through a patient's mouth and into the patient's windpipe, and forms an airtight seal on top of a patient's glottis, allowing a secure airway to be managed by a physician. In other words, LMAs are designed to reduce the risk of improperly placing an endotracheal tube into the esophagus rather than the trachea.

FIG. 1 illustrates a commonly used LMA 100. The conventional LMA 100 according to FIG. 1 includes a mask 102 that can be surrounded by a cuff or balloon 102a which is inflatable via a balloon port 108 through a tubing 104. The mask 102 also includes an opening 102b therein for air to pass through. The balloon 102a is generally inflated once the LMA 100 is properly secured into a patient's mouth/pharynx. A ventilation/airway tube 106 is used for ventilation for the patient, and is connected to the opening 102b in the mask 102 at one end thereof, and is connected to a ventilator (not illustrated) at an opposite end thereof when in operation. The mask 102 and balloon 102a combination is generally inserted into the pharynx of a patient, this is sometimes accomplished with the aid of a laryngoscope (see FIG. 3), and when positioned in the patient's pharynx, the mask 102 seals around a patient's glottis with the aid of the balloon 102a.

FIG. 2 illustrates the LMA 100 placed correctly through the patient's mouth and into the patient's larynx. More specifically, the mask 102 is inserted through the patient's mouth and disposed above the patient's esophagus (ES) so that the opening 102b of the mask 102 is disposed below the patient's epiglottis (E) and in alignment with the patient's laryngeal inlet. Once the LMA device 100 is seated surrounding the laryngeal inlet, air is passed through the tube 104 to fill the balloon 102a, which in turn seals around the patient's laryngeal inlet to permit ventilation to the patent's lungs through the trachea (T) while preventing inhalation of gastric fluids into the patient's lungs.

With the LMA 100 it is difficult for a physician (or clinician) to determine whether the placement thereof is accurate. As a result, there are several risks of injury or death to the patient that can occur. For example, if the LMA 100 is not properly positioned, gastric acid present in vomit may enter into and damage the patient's lungs, or brain damage or death from lack of oxygen can occur within a short period of time if proper ventilation to the lungs cannot be achieved. Also, as pointed out above, with the LMA 100 an endoscope, or fiberoptic scope, is sometimes used to ensure proper placement. The endoscope or fiberoptic scope has a disadvantage that it requires considerable skill and time, as well being limited in control of the end of the scope once the end of the scope enters the patient's trachea.

FIGS. 3A and 3B illustrate an intubating laryngeal mask airway device 30 (ILM) disclosed in U.S. Publication No.: 2006/0162730 A1. This ILM device 30 includes an airway tube 31 attached to a mask portion 32. The mask portion is surrounded by an elliptical cuff 33. The ILM device 30 also includes video sensors 42 and illumination source 43 disposed and fixed within a bowl of the mask 32. The video sensors 42 are disposed at an angle to offer a view of the larynx while the illumination source 43 provides light. The cuff 33 can be inflated by a flow of air through a tube 35 to the cuff 33. The video sensors 42 and illumination source 43 are connected to a video monitor 24 via electrical leads 44 and a connector 45. The electrical leads 44 are fed through the airway tube 31 in which oxygen flows to and from a patient to help the patient breath.

In order to attempt to obtain a better view of a patient's larynx a handle 39 is attached to one end of the airway tube 31, which allows for repositioning the entire ILM in the patient's throat. Since the video sensors 42 are fixed within the bowl of the mask 32, the only option for obtaining a different view of the patient's larynx is by moving the entire ILM with the externally disposed handle 39 during a procedure to resituate the angle of the video sensors.

FIG. 4 illustrates the use of a flexible endoscope 400 that is commonly used to monitor the interior of a patient's trachea as an LMA, such as the LMA 100 illustrated in FIG. 1, is being inserted through the patient's mouth and into the larynx. The endoscope 400 can be fed through the ventilation tube 106 so that a camera head 402 of the scope 400 extends through an opening 102b in the mask 102. The camera head 402 can video the trachea of a patient as the LMA 100 is being positioned in the patient's larynx so that proper insertion can be performed. However, the endoscope 400 has a limited view of the interior of a patient's trachea due to the limited peripheral view of the camera head 402 as well as the limited control of the camera head 402 as it extends out of the mask opening 102b and into the larynx. As a result of the limited view and control of the camera head 402 at the tip of the endoscope 400, it is difficult to determine with certainty whether the LMA 100 is properly seated so that the trachea is safely isolated from the esophagus. With this system it is also difficult to obtain an accurate view of a desired portion of a patient's trachea in order to monitor an incision into the trachea and insertion of a tracheostomy tube during a tracheostomy procedure.

Moreover, when inserting a flexible endoscope 400 through a ventilation tube of an LMA, one doctor/clinician is required to property manipulate the LMA while a second doctor/clinician is required to manage the flexible fiberoptic scope 400 itself in order to attempt to obtain a desired view of the patient's larynx and trachea once the scope 400 exits the ventilation tube of the LMA.

FIG. 5 illustrates a commonly used endotracheal tube 500. The endotracheal tube (ET) 500 is currently used to clear a patient's air passage while closing off access to the esophagus so that saliva and/or other foreign matters cannot enter into the trachea from the patient's stomach. The endotracheal tube 500 is generally a flexible plastic tube that is placed into a patient's mouth and then down into the trachea (airway). A physician inserts an endotracheal tube with the help of a laryngoscope, in a procedure called endotracheal intubation. The purpose of using an endotracheal tub is to ventilate a patient's lungs. The endotracheal tube 500 is inserted with the aid of a laryngoscope 502 to help the physician properly insert the tube 500 into the patient's trachea and avoid the esophagus. A balloon inflator 504 that connects to a balloon 506 disposed about 2 cm from a distal tip of the ET tube. The balloon 506 is inflated once the ET tube is inserted to ensure a tight seal of the ET tube against the tracheal wall.

However, insertion of an endotracheal tube 500 into a patient's trachea during an endotracheal intubation procedure is often only the first step during either an emergency or elective procedure to help a patient breath. A second step, referred to as a tracheostomy, is often performed, again either electively or emergently, on an patient who is unconscious, when an patient's airway is restricted in many possible ways, when the airway is blocked or damaged, or when a disease or other problem makes normal breathing impossible. The tracheostomy requires creating an opening below vocal cords in the neck of a patient by creating an incision in the neck with a scalpel. The opening is formed in order to place a breathing tube, referred to as a tracheostomy tube, into the patient's windpipe through the opening. This allows air to enter the lungs while bypassing the mouth, nose, and throat.

In order to perform a percutaneous tracheostomy, the physician must be able to see the inside of the patient's trachea to determine whether a needle used to inject anesthesia is properly positioned and whether an incision is properly formed. More specifically, a local anesthetic is first injected with a needle at the area of the neck where the trachea is located. The physician must be able to see how far the needle has been inserted through the patient's neck to ensure that the anesthetic is properly injected. Next, the physician must be able to see that the scalpel is properly used to make the cut in the patient's trachea to a proper depth and location. The physician must also insert a guidewire into the tracheal lumen in order to guide insertion of the tracheostomy tube.

Unfortunately, performing a percutaneous tracheostomy procedure using the endotracheal tube 500 as illustrated in FIG. 5 is limited due to the tube's limited ability to aid a physician in preparation for a tracheostomy. A bronchoscope, which is a device used to examine the bronchial airways is often used to guide the tracheostomy procedure. The bronchoscope is inserted through the endotracheal tube 500. The endotracheal tube 500 is then withdrawn by a certain amount to allow for viewing of tracheal lumen since the endotracheal tube 500 would normally occupy the position needed for viewing. This procedure can lead to complications such as dislodgment of the endotracheal tube 500 completely. This also requires 2 operators, one to operate the bronchoscope and another to hold the endotracheal tube in the correct position. Since the bronchoscope is fixed at a certain position the bronchoscope has a limited viewing angle and can only provide the physician with a view of the front of the trachea. Moreover, by the time the ET tube 500 is fully inserted into the patient's trachea, the bronchoscope is past the position in which a needle for providing anesthesia must be inserted as well as the position in which a scalpel must make a cut in the patient's neck to form an opening to insert a breathing tube. This limitation makes the preparation for performing a tracheostomy very difficult and cumbersome. Furthermore, mistakes in application of a needle for providing anesthesia or insertion of the guide wire can have devastating effects on the patient, and mistakes in forming an accurate incision into the patient's neck and into the trachea can cause permanent damage or even death to the patient.

In view of the foregoing, there is a recognized need for a visual assistance system to accurately place an LMA through a patient's mouth and to the trachea, and for a visual assistance system to accurately guide a physician to apply anesthesia to an patient prior to performing a tracheotomy procedure as well as accurately performing the tracheotomy procedure itself.

There is also a recognized need to provide a system which can be operated by a single physician/clinician in order to properly and simultaneously insert an LMA through a patient's mouth and into the patient's trachea while being able to continuously view any desired portion of the patient's trachea so that a percutaneous tracheostomy is properly performed.

SUMMARY OF THE INVENTIVE CONCEPT

The present general inventive concept provides a tracheoscope control device, a laryngeal mask airway (LMA) device, and a combination system thereof that can control a distal end of a tracheoscope while disposed in the larynx of a patient. More particularly, the present inventive concept relates to a tracheoscope control device, a laryngeal mask airway device, and a combination system thereof that can articulate a camera disposed at a distal end of a tracheoscope by an angular range of at least 180 degrees and can lock the camera head at any desired angle while disposed at a patient's tracheal tube.

Additional features and utilities of the present general inventive concept will be set forth in part in the description which follows and, in part, will be obvious from the description, or may be learned by practice of the general inventive concept.

The foregoing and/or other features and utilities of the present general inventive can be achieved by providing a tracheoscope control device, comprising: an elongated hollow body including first and second axially aligned insertion holes extending through opposite sides thereof; an articulation lever disposed at one side of the body and having a hole extending through one end thereof, the hole having a key-type groove formed therein; an anchor having a head portion and a tubular body connected at one end to the head portion and having threads formed therein, the tubular body extending through the first axially aligned insertion hole, the anchor including: a key type extension formed at an end of the tubular body opposite the end connected to the head portion to engage with the key type groove in the articulation lever, and an articulation piece having a middle portion integrally formed with a middle portion the tubular body; a screw having threads formed along the body portion, the screw extending through the hole in the articulation lever, through the second axially aligned insertion hole and frictionally engaging with the threads in the tubular body of the anchor to engage the key type extension of the anchor with the key-type groove in the lever and create a frictional engagement between the lever and the elongated body; and a tracheoscope including a first end disposed inside the hollow body and a second end disposed outside the hollow body and configured to capture external videos, the tracheoscope further including a pair of wires extending along opposite sides thereof, the first end of the wires being connected to opposite ends of the articulation piece and the second end of the wires being connected adjacent to the second end of the scope at opposite sides thereof.

In an exemplary embodiment the device may further comprise a semiconductor chip disposed therein and including at least one processor to process video signals, the semiconductor chip being connected to the first end of the tracheoscope to receive the captures videos and to transmit processed video signals to an external display.

In another exemplary embodiment, the device may further comprise a camera disposed at the second end of the tracheoscope to capture videos.

In another exemplary embodiment, the device may further comprise a sheathing extending from the elongated hollow body to receive the tracheoscope therethrough and including two stationary tubes extending therethrough, each tube receiving a respective one of the wires therethrough such that when the articulation lever is rotated the wires slide through the respective tubes.

In still another exemplary embodiment, the device may further include a suction channel including two sections, a first end of a first section extending from a connector disposed at a suction hole formed through the elongated hollow body, and a first end of a second section extending through the sheathing alongside the tracheoscope and terminating adjacent the second end of the tracheoscope; and a suction button extending from the body at an angle substantially perpendicular to the axis extending through the pair of insertion holes, the suction button including: a first button portion extending outside the body and being configured to be pushed inward, and an air switch disposed inside the body and connected to a second end of the first section of the suction channel and to a second end of the second section of the suction channel such that when the button is pushed inward the air switch connects air flow between the first and second sections of the suction channel.

In still another exemplary embodiment, the screw threads may be formed of a flexible material that creates a friction with the corresponding threads of the anchor such that the screw threads do not move with respect to the anchor threads until a predetermined amount of rotational force is applied to the screw In yet another exemplary embodiment, the device may further include a flexible lever engagement unit having a hole extending through a middle thereof and including: a back part press-fit against an insertion hole and disposed inside the hollow body, and a front part connected to the back part, the front part being press-fit against the insertion hole and disposed outside the hollow body, the front part causing a frictional resistance to rotational movement of the articulation lever with respect thereto.

In still another exemplary embodiment, the flexible lever engagement unit may further comprise a plurality of bumps disposed along a surface of the front part, the bumps being configured to engage with bumps formed along a periphery of the hole in the articulation lever to mesh with the bumps on the articulation lever to provide a resisting force of rotation of the articulation lever with respect to the flexible lever engagement unit.

The foregoing and/or other features and utilities of the present general inventive can also be achieved by providing a laryngeal mask airway (LMA) device, comprising: an elongated body having an opening at a first end thereof configured to receive a ventilation tube and a second end thereof formed in a shape of a dome with a cuff surrounding the outer circumference of the dome, the cuff being configured to have a portion thereof rest at and block an esophagus, the body further including: a ventilation channel extending the entire length of the body from the opening at the first end thereof through a center portion of the dome; and a tracheoscope channel extending alongside and separate from the ventilation channel, the tracheoscope formed through a side of the body opposite a side in which the cuff rests at the esophagus such that a tracheoscope frictionally extends through tracheoscope channel and into a trachea.

In an exemplary embodiment, the LMA the device is formed of a silicone material.

The foregoing and/or other features and utilities of the present general inventive can also be achieved by providing a tracheoscope control device, comprising: an elongated hollow body configured to be gripped with one hand; a flexible lever engagement unit fixed within a hole extending through one side of the hollow body and including a hole through a middle thereof; an articulation lever including a first portion to be manipulated and a second portion frictionally engaged with a side of the lever engagement unit extending outside the hollow body such that a resistance is applied to the second portion thereof by the lever engagement unit when a predetermined force is applied to the first portion; an anchor rotatably engaged with and extending through a side of the hollow body opposite the articulation lever, the anchor including: a head portion disposed at the exterior surface of the hollow body, a tubular body portion extending from the head portion into the hollow body and connected to the second portion of the articulation lever and configured to rotate therewith, and an articulation piece integrally connected across to the tubular body portion and rotatable therewith; a tracheoscope having a first end disposed inside the hollow body, a middle portion extending through a bottom of the hollow body and a second end disposed outside the hollow body and including a camera attached thereto to capture videos; and a pair of wires extending along opposite sides of the tracheoscope, the wires having first ends connected to opposite ends of the articulation piece and second ends connected adjacent to the second end of the tracheoscope at opposite sides thereof such that application of a predetermined force to rotate the articulation lever articulates the articulation piece to move the camera about an angular range of 180 degrees In an exemplary embodiment, the second portion of the articulation lever may include a tubular body portion extending therefrom and having circular ribs in parallel and surrounding the tubular body portion along the length thereof, and a key engagement groove extending along the length thereof through the circular ribs; and the tubular body portion of the anchor may include circular ribs formed in parallel inside and along the length thereof and a key type extension extending portion extending along the length thereof through the circular ribs such that insertion of the second portion of the articulation lever into the tubular body portion of the anchor locks the second portion of the articulation lever inside the tubular body portion, creates a frictional rotational resistance between the articulation lever and the lever engagement unit and forces the tubular body portion to rotate when the second portion of the articulation lever is rotated.

In an exemplary embodiment, the flexible lever engagement unit may further include a plurality of bumps disposed along a surface facing the second portion of the articulation lever, the bumps being configured to engage with bumps formed along a surface of the second portion of the articulation lever to mesh therewith to provide a frictional rotational resistance of the articulation lever with respect to the flexible lever engagement unit The foregoing and/or other features and utilities of the present general inventive can also be achieved by providing a tracheoscope control system, comprising: an elongated hollow body configured to be held with one hand; a flexible lever engagement unit fixed within a hole extending through one side of the hollow body; an articulation lever including a first portion to be manipulated and a second portion engaged with and frictionally rotatable with respect to a side of the lever engagement unit when a predetermined force is applied to the first portion; an anchor rotatably engaged with and extending through the surface of the hollow body opposite the articulation lever, the anchor including: a head portion disposed at the exterior surface of the hollow body, a tubular body portion connected to the head portion and extending into the hollow body and being connected to the second portion of the articulation lever to rotate therewith, and an articulation piece integrally connected to the tubular body portion and rotatable therewith; a tracheoscope having a first end disposed inside the hollow body, a middle portion extending through a bottom of the hollow body and a second end external to the hollow body and including a camera attached thereto to capture videos; and a pair of wires extending along opposite sides of the tracheoscope, the wires having first ends connected to opposite ends of the articulation piece and second ends connected adjacent to and at opposite sides of the second end of the tracheoscope such that application of a predetermined force to rotate the articulation lever and the articulation piece and articulates the camera about an angular range of at least 180 degrees; a laryngeal mask airway (LMA) device, including: a flexible body including a first end having an opening configured to receive a ventilation tube and a second end formed in a shape of a dome with a cuff surrounding the outer circumference of the dome, the cuff being configured to have a portion thereof rest at and block an esophagus, a ventilation channel extending from the opening at the first end through a center portion of the dome; and a tracheoscope channel extending the entire length of the flexible body and adjacent to the ventilation channel, the tracheoscope channel frictionally containing a portion of the tracheoscope adjacent the second end thereof such that the camera extends past the dome of the LMA device.

In an exemplary embodiment, the second portion of the articulation lever may include a tubular body portion extending therefrom and having circular ribs in parallel and surrounding the tubular body portion along the length thereof, and a key engagement groove extending along the length thereof through the circular ribs; and the tubular body portion of the anchor may include circular ribs formed in parallel inside and along the length thereof and a key type extension extending portion extending along the length thereof through the circular ribs such that insertion of the second portion of the articulation lever into the tubular body portion of the anchor locks the second portion of the articulation lever inside the tubular body portion, creates a frictional rotational resistance between the articulation lever and the lever engagement unit and forces the tubular body portion to rotate when the second portion of the articulation lever is rotated.

In another exemplary embodiment, the flexible lever engagement unit may further include a plurality of bumps disposed along a surface facing the second portion of the articulation lever, the bumps being configured to engage with bumps formed along a surface of the second portion of the articulation lever to mesh therewith to provide a frictional rotational resistance of the articulation lever with respect to the flexible lever engagement unit The foregoing and/or other features and utilities of the present general inventive can also be achieved by providing a method of controlling a distal end of tracheoscope with respect to a proximal end disposed within a tracheoscope control device, the method comprising: holding the tracheoscope control device in one hand while rotating, with a thumb of the one hand, an articulation lever about a frictional lever engagement unit formed through a side of the tracheoscope control device; rotating an articulation piece disposed inside the tracheoscope control device with the rotational force of the articulation lever; articulating a distal end of a tracheoscope disposed outside the tracheoscope control device about an angular range of at least 180 degrees with the rotational force of the articulation piece; and locking the distal end of the tracheoscope with the frictional engagement between the articulation lever and the frictional lever engagement unit by stopping the rotation of the articulation lever In an exemplary embodiment, the method may further include supporting a length of the tracheoscope within a tightly fit channel formed through a laryngeal mask airway (LMA) device, the tightly fit channel extending adjacent to but separate from a ventilation channel such that the distal end of the tracheoscope extends past an end of the LMA device be a predetermined distance.

The foregoing and/or other features and utilities of the present general inventive can also be achieved by providing a laryngeal mask airway (LMA) device, comprising: an elongated body including a ventilation channel extending the entire length thereof; and a second channel extending alongside and separate from the ventilation channel, the second channel being formed to have a diameter substantially the same as a diameter of a scope to be inserted therethrough such that a length of the scope within the second channel remains at a fixed position therein while distal of the scope that extends out of the second channel can be manipulate to move by control device at the proximal end of the scope.

The foregoing and/or other features and utilities of the present general inventive can also be achieved by providing a tracheoscope control device, comprising: an elongated body configured to be held in one hand of an operator, the body including: a rotation resistant engagement unit connected at a side of the body; an articulation lever rotationally fixed to the body through the rotation resistant engagement unit, the articulation lever being rotatable upon a predetermined force that overcomes the rotation resistance of the rotation resistant engagement unit; a tracheoscope including a first end disposed inside the body and a second end disposed outside the body and configured to capture external videos; and a pair of wires extending along opposite sides of the tracheoscope, a first end of the wires being connected to a portion of the articulation lever disposed inside the body and second ends of the wires being connected at opposite sides of the second end of the tracheoscope.

BRIEF DESCRIPTION OF THE DRAWINGS

These and/or other features and utilities of the present general inventive concept will become apparent and more readily appreciated from the following description of the embodiments, taken in conjunction with the accompanying drawings of which.

DETAILED DESCRIPTION OF THE PREFERRED EMBODIMENTS

Figure 1:
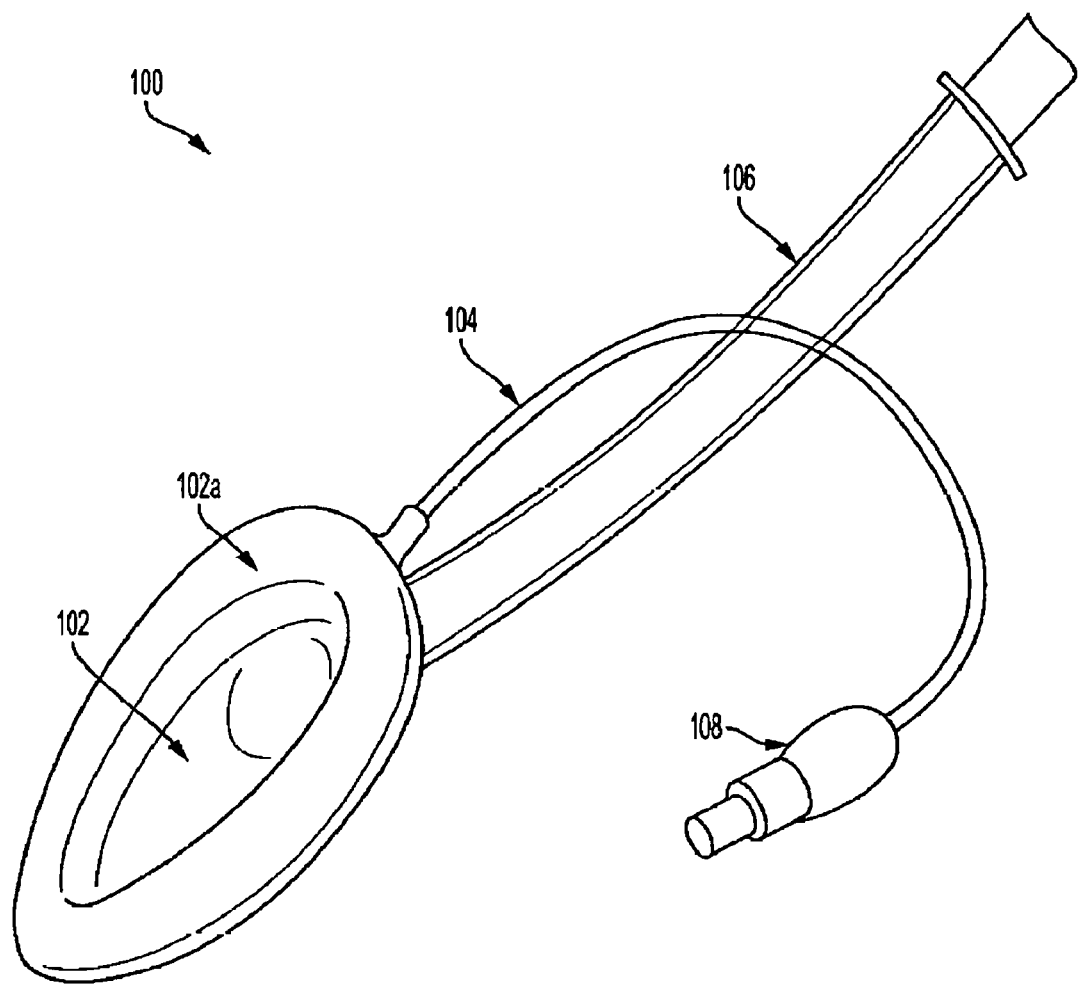
FIG. 1 illustrates a conventional laryngeal mask airway (LMA) device.
Figure 2:
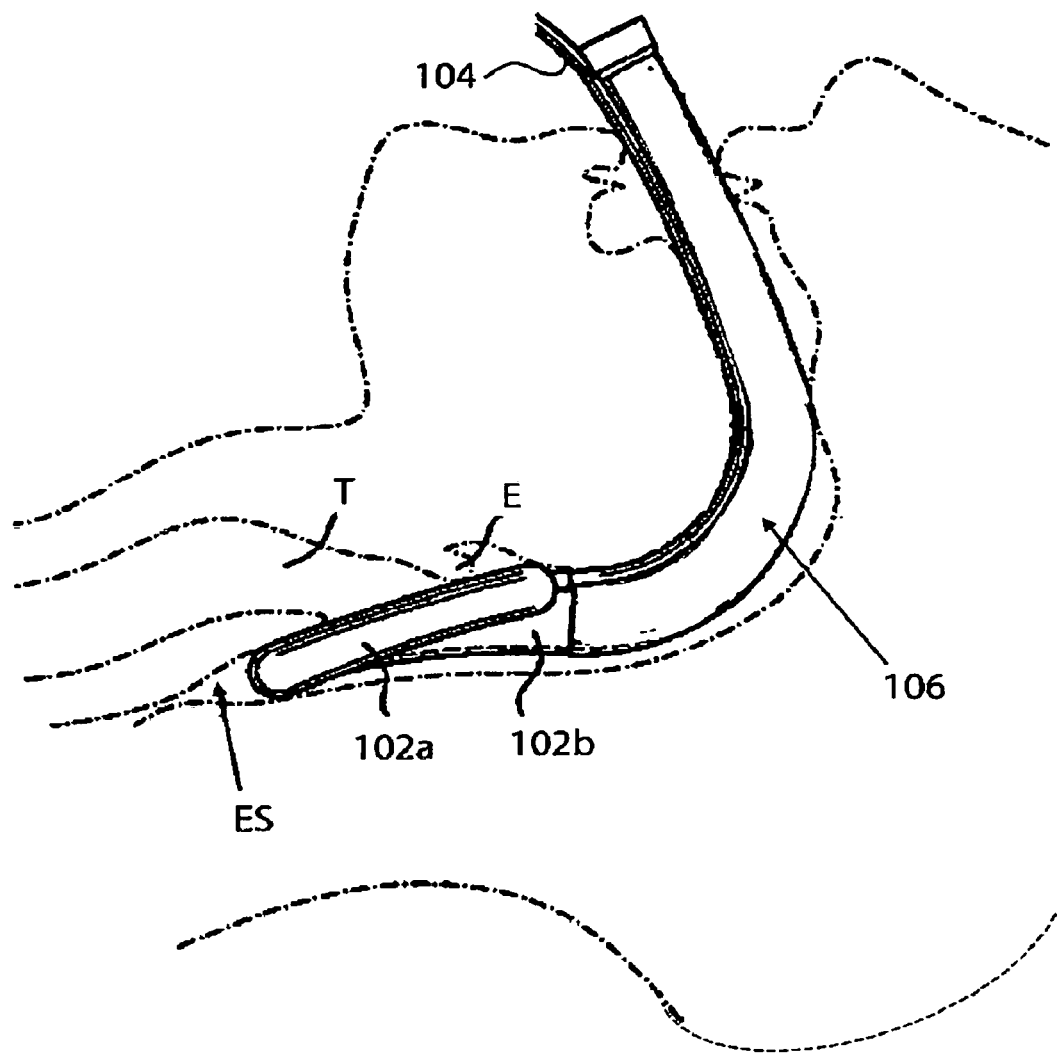
FIG. 2 illustrates an operational view of another conventional laryngeal mask airway (LMA) device.
Figure 3A:
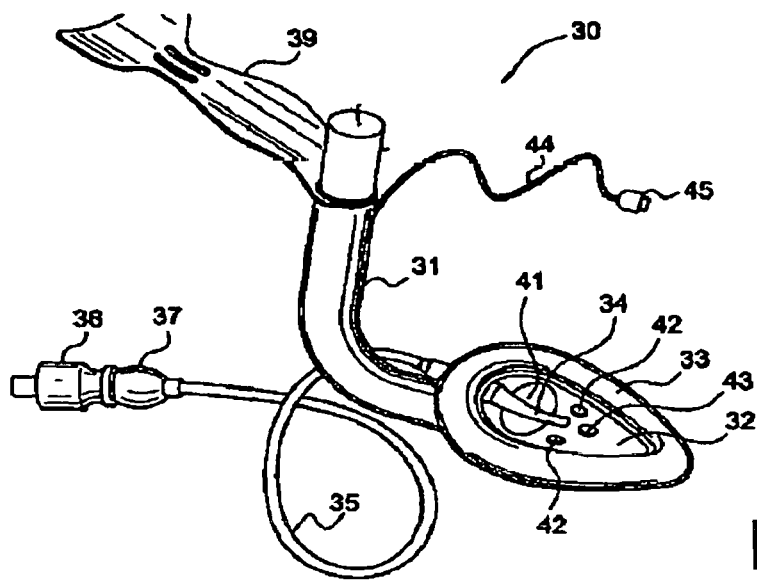
FIG. 3A illustrates another conventional laryngeal mask airway (LMA) device.
Figure 3B:
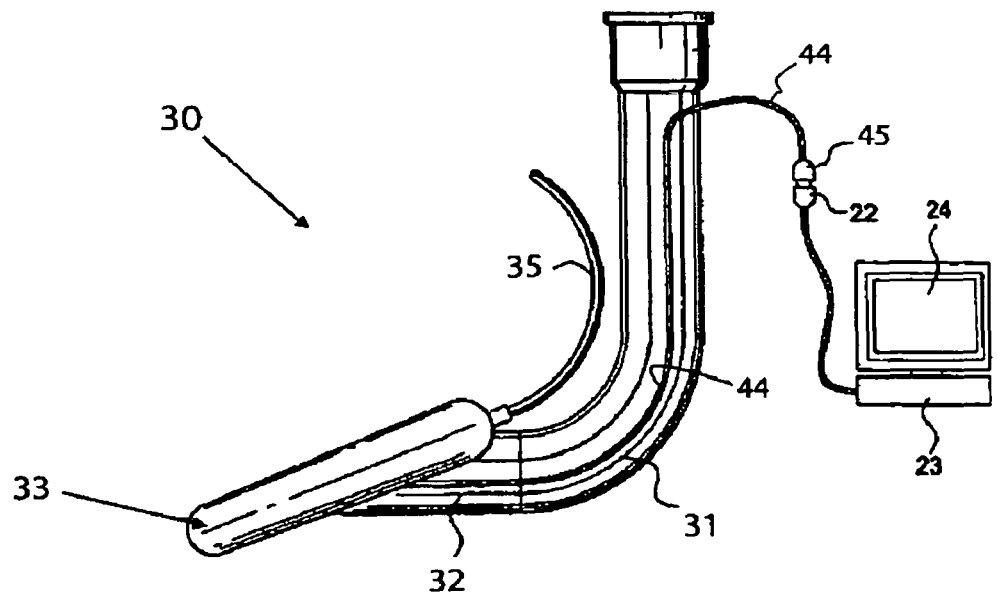
FIG. 3B illustrates still another conventional laryngeal mask airway (LMA) device.
Figure 4:
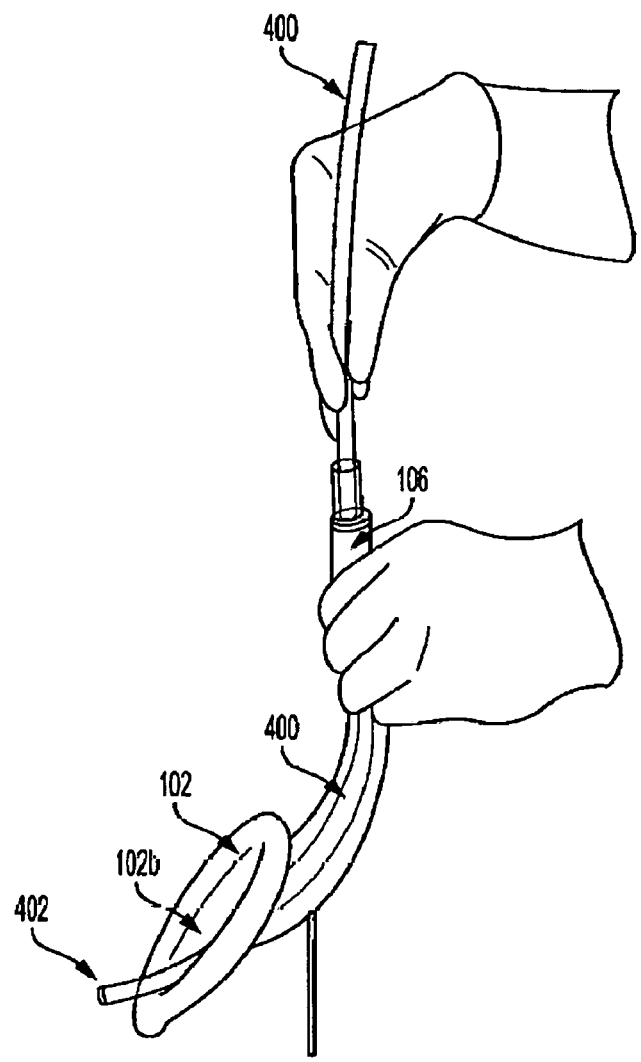
FIG. 4 illustrates operational use of a combinational use of a conventional tracheoscope and conventional laryngeal mask airway (LMA) device.
Figure 5:
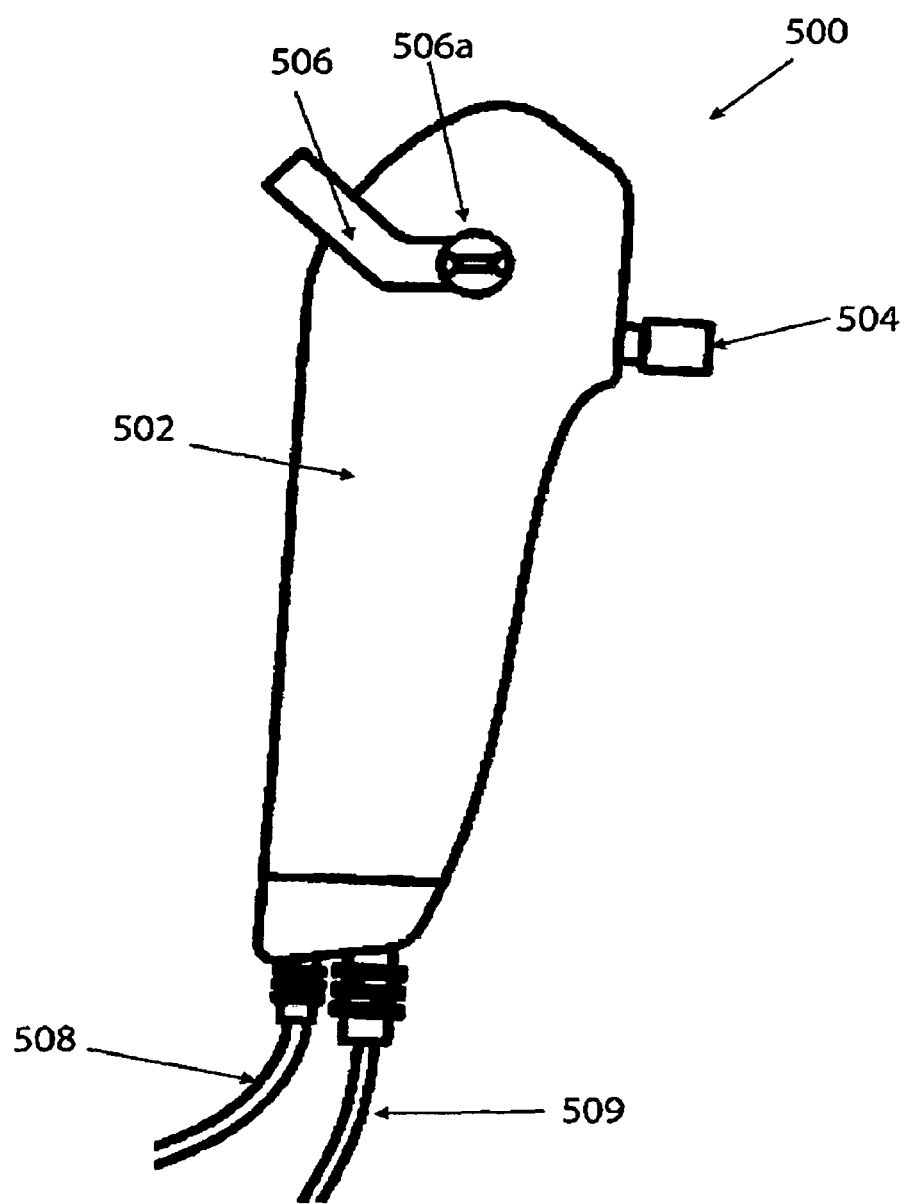
FIG. 5 illustrates an operational use of a conventional endotracheal tube.

Reference will now be made in detail to the embodiments of the present general inventive concept, examples of which are illustrated in the accompanying drawings, wherein like reference numerals refer to the like elements throughout. The embodiments are described below in order to explain the present general inventive concept while referring to the figures. Also, while describing the present general inventive concept, detailed descriptions about related well-known functions or configurations that may diminish the clarity of the points of the present general inventive concept are omitted.

It will be understood that although the terms "first" and "second" are used herein to describe various elements, these elements should not be limited by these terms. These terms are only used to distinguish one element from another element. Thus, a first element could be termed a second element, and similarly, a second element may be termed a first element without departing from the teachings of this disclosure.

Expressions such as "at least one of," when preceding a list of elements, modify the entire list of elements and do not modify the patient elements of the list.

All terms including descriptive or technical terms which are used herein should be construed as having meanings that are obvious to one of ordinary skill in the art. However, the terms may have different meanings according to an intention of one of ordinary skill in the art, case precedents, or the appearance of new technologies. Also, some terms may be arbitrarily selected by the applicant, and in this case, the meaning of the selected terms will be described in detail in the detailed description of the invention. Thus, the terms used herein have to be defined based on the meaning of the terms together with the description throughout the specification.

Also, when a part "includes" or "comprises" an element, unless there is a particular description contrary thereto, the part can further include other elements, not excluding the other elements.

Hereinafter, one or more exemplary embodiments of the present general inventive concept will be described in detail with reference to accompanying drawings.

Exemplary embodiments of the present general inventive concept are directed to a tracheoscope control device, a laryngeal mask airway (LMA) device, and a combination system thereof to assist in accurate placement of the LMA device and to accurately monitor an anesthesia application and a tracheostomy procedure. More particularly, the present inventive concept relates to a tracheoscope control device, a laryngeal mask airway (LMA) device, and a combination system thereof that provides a camera head that can articulate about an angular range of at least 180 degrees and can lock the camera head at any desired angle within a patient's larynx to monitor the patient's trachea during application of anesthesia and during a tracheostomy procedure.

FIG. 6A illustrates a side view of a tracheoscope control device 600 according to an exemplary embodiment of the present inventive concept. A tracheoscope is a present invention by the Applicant, which is different from an endoscope which is conventionally used to view a patient's larynx or trachea. The tracheoscope, as described herein and used together with the presently invented tracheoscope control device 600 provides many advantages over the conventionally used endoscope, a discussed below.

The tracheoscope control device 600 can include a body 602 having a shape that conforms to an patient's hand such that the tracheoscope control device 600 can be held in one hand of a physician, clinician, or other operator of the device 600 while the a tracheoscope is articulated by a thumb of the hand. The shape of the body 602 shape can be varied in order to, for example conform to different size hands of a physician, to include separate grooves to accommodate a physician's fingers, or for other conveniences of an operator's hand without departing from the principles and spirit of the present overall inventive concept.

The body 602 of the tracheoscope control device 600 can include a first side 602a and a second side 602b that can be connected together to form the entire body 602. First and second sides 602a and 602b can each include a pair of axially aligned insertion holes 602c, such that when the first side 602a and the second side 602b are connected together, two axially aligned insertion holes 602c are formed. As illustrated in FIG. 6A, one of the insertion holes 602c can be provided to receive a screw 608 therethrough which can fasten a tracheoscope articulation lever 606 to the body 602. The screw 608 can include a head 608a and a body portion 608b (see FIG. 7). The body portion 608b of the screw 608 preferably includes semi-flexible threads along a length thereof which will create a frictional engagement with opposing threads. Since the threads are semi-flexible, the threads of the screw 608 will create more friction with the opposing threads as the screw 608 is tightened. This frictional screw 608 can be inserted through a hole at one end of the articulation lever 606, through the corresponding insertion hole 602c and then fastened to the body 602 by engaging the threads thereof with corresponding threads disposed in the body 602 to rotatably connect the articulation lever 606 to an outer surface of the body 602.

The articulation lever 606 can be frictionally pressed against the body 602 of the articulating tracheoscope device 600 by a pressure against the articulation lever 606 caused by the threads of the frictional screw 608 frictionally engaging with corresponding threads within the body 602 as the screw 608 becomes more tightened. According to an exemplary embodiment, tightening of the frictional screw 608 will cause the articulation lever 606 to become frictionally pressed against the body 602 such that frictional engagement with the body 602 will cause the articulation lever 606 to remain where positioned until a certain amount of pressure required to overcome the frictional engagement is applied to the articulation lever 606.

The frictional screw 608 can be formed of a flexible plastic such that when the screw 608 is threaded fully into a corresponding set of threads, the threads of the frictional screw 608 bend or flex by a certain amount which causes a friction with the corresponding threads, thus preventing the frictional screw 608 from turning without a predetermined amount of force applied thereto.

The frictional screw 608 can include a groove 608a1 extending outward across a center of the screw head 608a. The groove 608a1 preferably extends outward by a sufficient amount to enable two fingers of an individual to turn the frictional screw 608, thus tightening and loosening the frictional screw 608 by gripping and rotating the frictional screw 608 by the groove 608a1 and applying a predetermined amount of rotational force to the frictional screw 608.

As will be discussed in more detail below, the frictional engagement of the articulation lever 606 against the body 602 caused by the frictional screw 608 can allow for numerous rotational locking positions of the articulation lever 606, and hence numerous locked angular positions of a distal end of a tracheoscope (described in more detail below).

The articulation lever 606 is not limited to being connected to the body 602 by use of a frictional screw 608, but instead can be frictionally connected to the body 602 by other means such as, for example by a lever engagement unit (see FIGS. 9A and 9B) that frictionally engages with both the body 602 and an end of the articulation lever 606. Alternatively, the articulation lever 606 can be connected to the body 602 by other means configurations which will provide the intended purposes of controlling the articulation lever as described herein.

FIGS. 6B and 6C illustrate an exemplary embodiment of a tracheoscope 601 with a camera 601a disposed at a terminating end of the tracheoscope 601. Also illustrated is a distal end (outside of the device 600) of a suction channel 604a. The suction channel 604a can extend alongside the tracheoscope 601. According to an exemplary embodiment, a pair of light emitting diodes (LEDs) 605 can also extend along the length of the tracheoscope 601 and terminate beside the camera 601a (see FIG. 6C).

A first end of the tracheoscope 601 can extend into the internal portion of the body 602 and a second end of the tracheoscope 601 can include the camera 601a (FIGS. 6B and 6C) connected thereto. The second end of the tracheoscope and camera 601a are configured to be inserted through an patient's mouth to view and/or video an patient's larynx and trachea.

A suction channel system 604 can also be disposed at a side of the body 602 and can include a first part having a suction button 604a connected thereto and extending outside the body 602, and an air switch 604b disposed inside the body and connected to a suction hole 603 which also extends outside the body 602. The air switch 604b can be disposed at a point along the suction channel 604a and operate to open and close an air flow through the suction channel 604a and the suction hole 603 when the suction button 604a is pressed. The button 604a can include a spring therein to allow the button 604a to spring back outward when released. The suction channel 604a can extend alongside the tracheoscope 601 and can suction fluid from an patient's larynx and/or trachea once the tracheoscope 601 and suction channel 604a are secured in a desired position. The tracheoscope 601 and suction channel 604a can be encased within a sheathing 612 (FIGS. 6B and 6C) for protection as well as for other purposes, as is described in more detail below Images and/or videos captured by the camera 601a disposed at the end of the tracheoscope 601 can be transmitted to a video monitor (see FIG. 11) through a video cable 610. Video signals transmitted by the tracheoscope 601 can be received and processes to be viewable at the monitor to allow a physician to view an patient's larynx and trachea on the monitor while performing one of many medical procedures.

Since the articulation lever 606 can be frictionally pressed to the body 602 by tightening the frictional screw 608, and therefore remain fixed at any desired position in which the articulation lever 606 is moved, a physician can place the tracheoscope control device body 602 down and readily have both hands free to conduct other operations, such as, for example performing the many other procedures required during a tracheostomy procedure, or other procedures.

Figure 6:
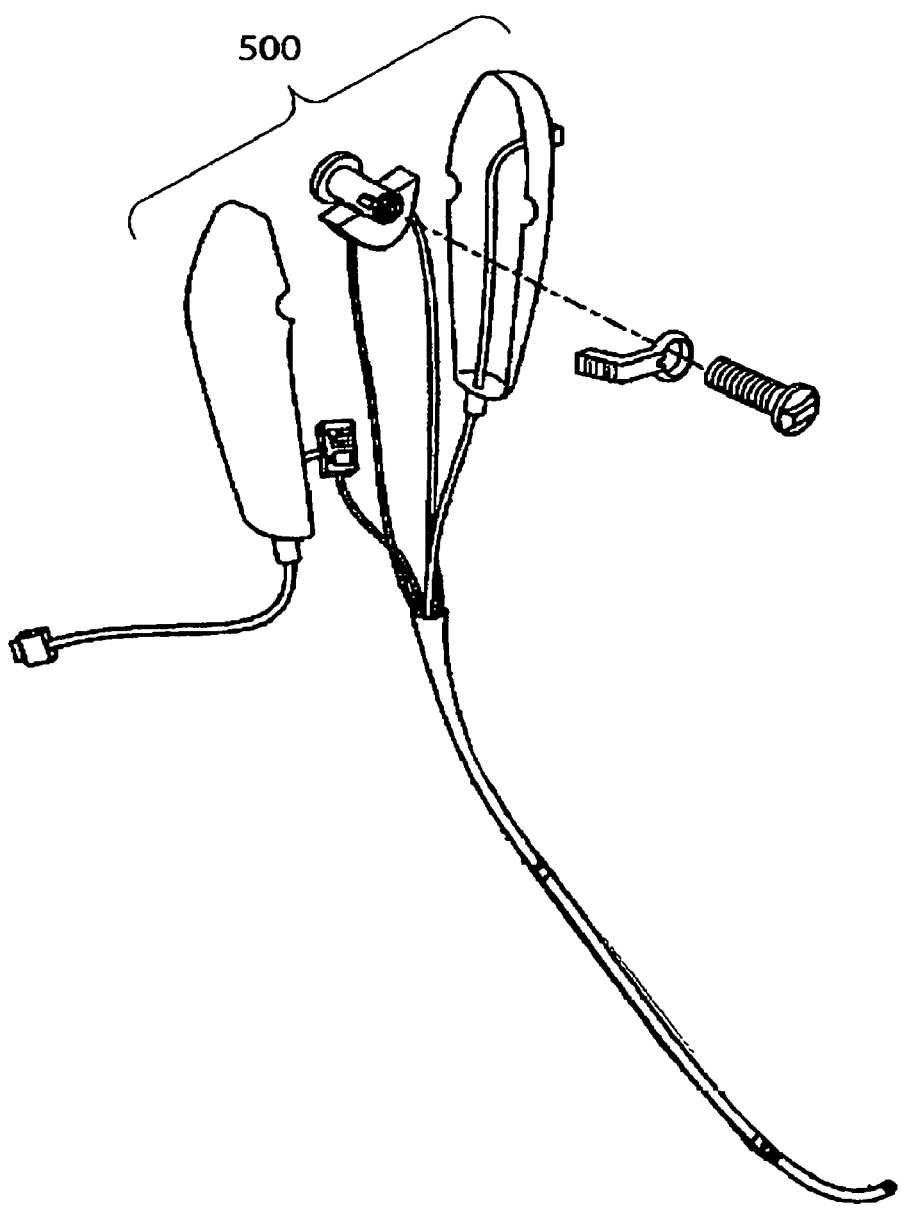
FIG. 6A illustrates a side view of a tracheoscope control device according to an exemplary embodiment of the present inventive concept.
FIG. 6B illustrates the lower portion of the articulating tracheoscope of FIG. 6A, according to an exemplary embodiment of the present inventive concept.
FIG. 6C illustrates an end view of the lower portion of the articulating tracheoscope of FIG. 6A.
Figure 7:
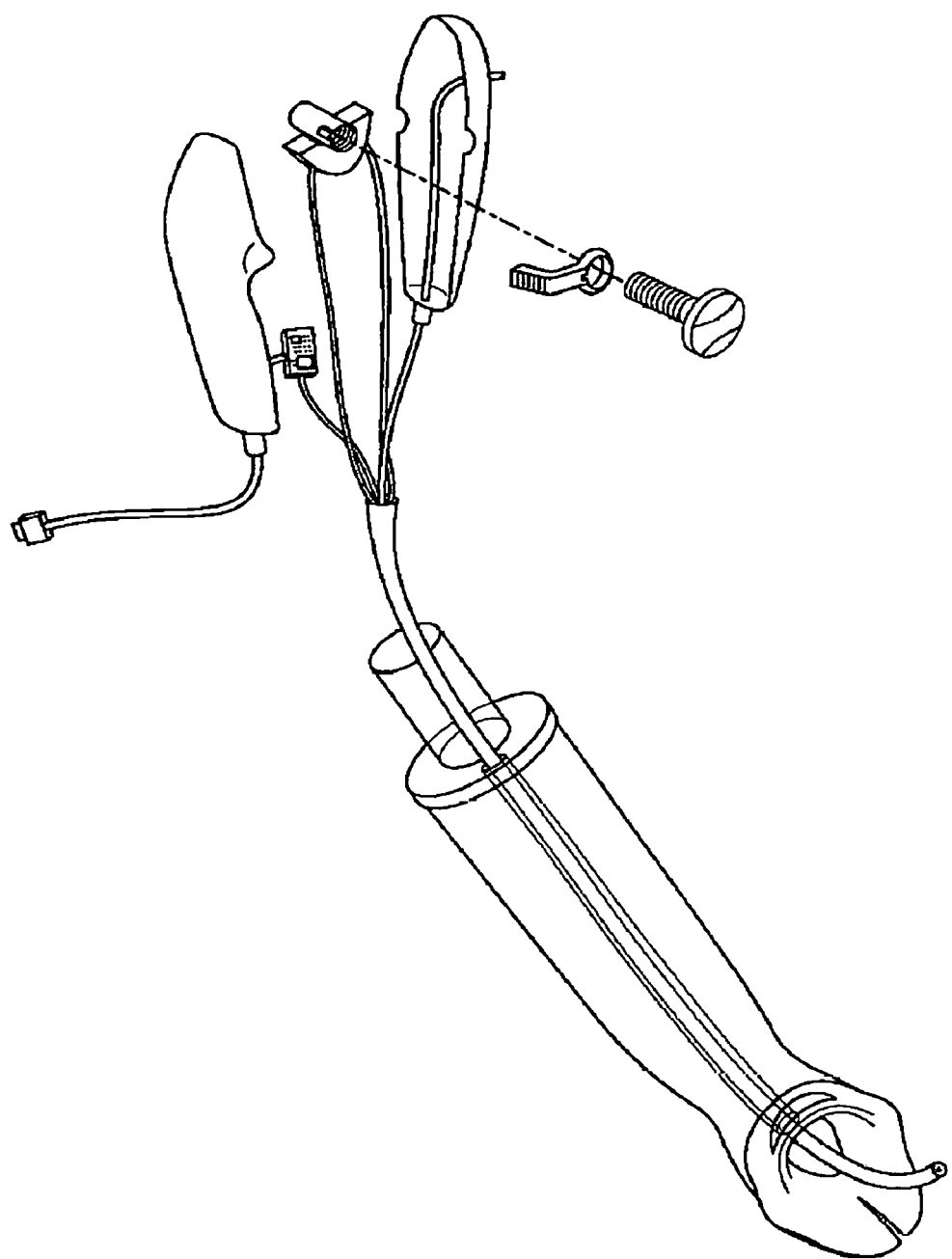
FIG. 7 illustrates an expanded view of a tracheoscope control device with an articulating tracheoscope according to the exemplary embodiment of FIG. 6A.

FIG. 7 illustrates an expanded plan view of an tracheoscope control device 600 according to the exemplary embodiment of FIG. 6A. The tracheoscope control device body 602 can be formed of two separate parts 602a and 602b that are connected together to form a body that can easily be held in one hand. The two parts 602a and 602b can each include a pair of axially aligned semicircular grooves that when connected together form two axially aligned holes 602c through the body 602.

The frictional screw 608 according to this exemplary embodiment can include semi-flexible threads extending along a body portion 608b thereof, the body portion 608b extending through one of the opposing insertion holes 602c to engage with threads of a corresponding internally threaded anchor 702. More specifically, the anchor 702 can include an internally threaded tubular body portion 702b and an external diameter that can extend through an insertion hole 602c opposite the insertion hole 602c in which the frictional screw 608 is inserted. At one end of the tubular body portion 702b can be a head 702a integrally formed thereto. The head 702a preferably has a diameter larger than a diameter of the corresponding insertion hole 602c such that when the body portion 608b of the frictional screw 608 engages with the internally disposed threads of the anchor body portion 702b, the screw head 608a and the anchor head 702a are blocked from passing through the respective insertion holes 602c.

The anchor body portion 702b can include an articulation piece 704 integrally connected to an outer surface thereof. The articulation piece 704 can be semicircular in shape as will be described in more detail below. The anchor body portion 702b can also include a key type extension 702c formed to extend outward at an end thereof opposite the end in which the head 702a is connected.

The articulation lever 606 can include a body portion 606a and an engagement portion 606b. The engagement portion 606b can be circular in shape with a hole through a center and can also include key engagement groove 606c that extends into a portion of the engagement portion 606b adjacent the hole. The key engagement groove 606c can be configured to receive and engage with the key type extension 702c of the anchor body portion 702b.

When the frictional screw 608 is fed through the hole in the engagement portion 606b of the articulation lever 606 and threaded into threads of the body portion 702b of the anchor 702, the articulation lever 606 and the anchor 702 become engaged with each other as a result of the key type extension 702c being inserted into and engaging with the key engagement groove 606c. At this point when the articulation lever 606 is moved back and forth by a physician/clinician, the anchor 702 and frictional screw 608 both securely rotate within the respective insertion holes 602c.

According to an exemplary embodiment, both the anchor 702 and the frictional screw 608 can be formed of a material that creates a frictional engagement between the corresponding threads, causing the screw body portion 608b to remain where rested along the threads within the tubular body portion 702b until a predetermined amount of force is applied to the screw head 608a to further rotate the frictional screw 608. In this exemplary embodiment, the physician or other operator can articulate the second end of the tracheoscope 601 and camera 601a to any desired position, at which point the physician can then tighten the frictional screw 608 by gripping and turning the groove 608a1 on the screw head 608a until the frictional screw 608 is tightly threaded into the anchor body 702b. Since the threads of the frictional screw 608 create a frictional engagement with the threads of the anchor 702, the frictional screw 608 will not move with respect to the anchor 702 without the predetermined amount of force applied by the physician or other operator to overcome the frictional force. Therefore, the physician can put down the tracheoscope control device body 602 and have both hands free to perform a next procedure.

Still referring to FIG. 7, a pair of wires 614 can be connected at one end to the semicircular articulation piece 704 at the circular portion thereof such that a first end of one of the wires 614 is connected at one end of the articulation piece 704 and a first end of the other wire 614 is connected at the other end of the articulation piece 704. The wires 614 can extend alongside the tracheoscope 601 within the sheathing 612. The sheathing 612 can include a pair of tubes (not illustrated) to receive a respective wire 614 therethrough in a sliding manner.

A second end of one of the wires 614 can be connected near the second end of the tracheoscope 601 and a second end of the other wire 614 can be connected near the second end of the tracheoscope 601 at an opposite side of the tracheoscope 601 from the side in which the first wire 614 is connected. The two wires 614 preferably extend along opposite sides of the tracheoscope 601.

As the articulation lever 606 is rotated in either a clockwise or counterclockwise direction by the predetermined force required to overcome the frictional engagement between the articulation lever 606 and the body 602, the anchor 702 moves together in rotation with the lever 606 due to the engagement of the key type extension 702c and the key engagement groove 606c, thus rotating the articulation piece 704 in unison with the articulation lever 606.

As the articulation lever 606 is rotated in a first direction (i.e. clockwise) by the required force applied thereto, the articulation piece 704 will rotate in the same direction and one of the wires 614 will be pulled by the articulation piece 704, thus pulling the second end of the tracheoscope 601 at the point where this wire 614 is connected to the tracheoscope 601. The pulling of the wire 614 on the second tracheoscope 601 will cause the second end of the tracheoscope 601 and the camera 601a to articulate in a first direction.

As the articulation lever 606 is rotated in an second direction (i.e., counterclockwise) by the required force applied thereto, the articulation piece 704 will rotate in the same direction. As a result, the other wire 614 will be pulled by the articulation piece 704, thus pulling the second end of the tracheoscope 601 at the point where this wire 614 is connected to the tracheoscope 601. The pulling of the wire 614 on the second end of the tracheoscope 601 will cause the second end of the tracheoscope 601 and the camera 601a to articulate in a second direction opposite the first direction. Accordingly, the second end of the tracheoscope 601 and the camera 601a can be articulated about an angular range of at least 180 degrees, thus providing a 180 degree view of the area in which the camera 601a is disposed.

When the camera 601a is positioned at a patient's trachea, the physician can move the articulation lever 606 by applying the required force to overcome the frictional engagement with the body 602. Since the articulation lever 606 is under this frictional engagement with the body 602 due to the tightening of the frictional screw 608, the articulation lever 606, tracheoscope 601 and camera 601a can all be moved together with precision to any desired position, and will remain at such a position in a locked state until the articulation lever 606 is once again moved by the force required to overcome the frictional engagement. Accordingly, the physician can rest the tracheoscope control device 600 down and perform a next procedure with both hands free to do so.

The signal generated by the camera 601a can be received by a semiconductor chip 706 provided within the body 602. The semiconductor chip can include one or more processors, including a video processor to process signals being received from the camera 601a. The processed video signals can then be transferred to an external monitor or other display device to continuously visually monitor the area in which the camera 601a is directed.

As described above, one or more light emitting diodes (LEDs) 605 (FIG. 6C) may also be extended along a side(s) of the tracheoscope 601 and terminate adjacent to the camera 601a to illuminate the area being captured by the camera 601a. The semiconductor chip 706 can include a processor to provide the signal for the LEDs 605.

Figure 8:
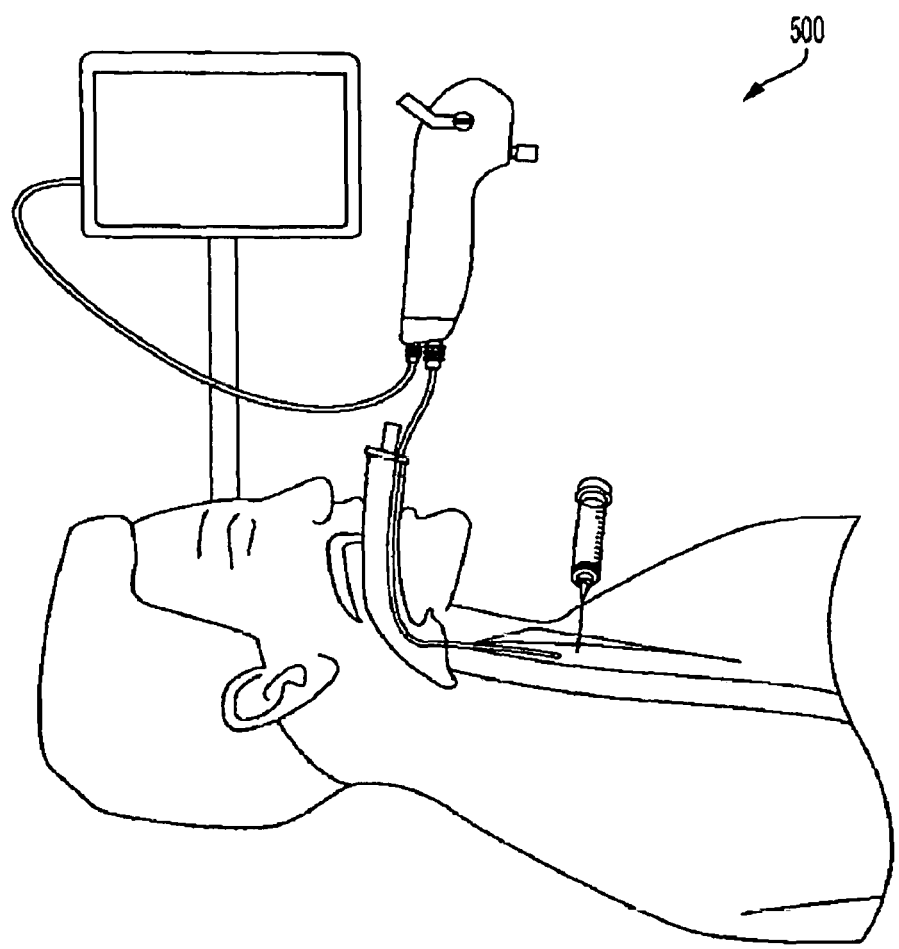
FIG. 8 illustrates a plan view of a laryngeal mask airway (LMA) device according to an exemplary embodiment of the present inventive concept.

FIG. 8 illustrates a laryngeal mask airway (LMA) device 800 according to an exemplary embodiment of the present inventive concept. The (LMA) device 800 is intended to be inserted into the throat of a patient to open the patient's airway to help the patient breath when such help is necessary. More specifically, a body portion 802 of the LMA 800 extends to a length sufficient to fit into a patient's mouth and throat and to the patent's trachea while an opposite end extends out of the patient's mouth to connect with a ventilation device. At one end of the body portion 802 can be formed a dome 804 surrounded by a cuff 806. The cuff 806 can be formed of a rubber or a silicone material which is capable of flexing so as not to damage the patient's throat, larynx or trachea. Alternatively, the cuff 806 and body portion 802 can be formed of any other type of material that will provide the intended purposes of providing stability to extend into the mouth and down the throat of a patient, while being flexible enough so that the cuff 806 does not cause damage to the patient's larynx or trachea. The entire LMA device 800 can also be formed of a rubber, silicone or other type of material that will performed the intended purposes of flexibly sliding into a patient's mouth, throat and larynx.

A ventilation hole 808 can be extended from a top portion of the LMA 800 through the middle portion of the body 802 and through the center of the dome 804. This ventilation hole 808 should have a diameter significantly large enough to allow a patient to receive and exhale enough oxygen to breath safely.

Conventionally, when an LMA device is positioned in a patient's throat, a tracheoscope or endoscopy scope is then inserted through a central ventilation hole/channel in the LMA, which allows the patient to breath. Since the ventilation hole in an LMA device must have a certain diameter to allow the patient to inhale and exhale enough oxygen to breath safely, the ventilation hole must be significantly larger than the scope that is conventionally fed through the ventilation hole. As a result of the requirement of the ventilation hole to have a fairly large diameter, a significant amount of space exists around the tracheoscope, resulting in the scope randomly wander from side to side. Moreover, when the distal end of the tracheoscope exits the other end of the LMA, there is no telling which direction the end of the tracheoscope will be pointing.

Accordingly, once the trachea/endoscopy scope is inserted through the LMA ventilation hole, retaining control of the end of the scope in which a camera is generally disposed is difficult to manage with any degree of accuracy. Thus a significant amount of maneuvering and manipulation by the physician is required, with both hands, to attempt to accurately position the tracheoscope so that the camera can video the parts of the patient's throat, larynx or trachea necessary to perform the required procedures. These important steps require more than one physician and/or clinician to hold the LMA in place, to feed the tracheoscope through the LMA ventilation hole, and to maneuver the tracheoscope to attempt to capture the desired part of a patient's trachea with the camera. When a tracheostomy procedure is necessary, this procedure can require up to three separate physicians and/or clinicians present to perform the entire procedure.

Still referring to FIG. 8, the body portion 802 of the LMA device 800 according to the present exemplary embodiment can include a second separate channel 810 that can be formed adjacent to the ventilation hole/channel 808 and extend the entire length of the body 802. The second channel 810 can be configured to tightly contain a portion of a tracheoscope 601 further be disposed at a position such that the sheathing 612 (including the tracheoscope 601, and will be referred to herein as a tracheoscope channel 810. The tracheoscope 601 (and possibly a suction channel, wires and LEDs) extends through the tracheoscope channel 810 and exits slightly past the cuff 806.

The tracheoscope channel 810 can be disposed lengthwise through the body 802 at a location such that the tracheoscope 601 will be spaced away from a patient's esophagus and closer to the patient's trachea so that the tracheoscope 601 and camera 601a will extend to the patient's trachea when the cuff 806 of the LMA device 800 is properly seated in the patient's larynx.

The tracheoscope channel 810 is preferably separate from the ventilation hole 808 and preferably has a diameter small enough that the sheathing 612 (enclosing at least one of the tracheoscope 601 and wires 614, the suction channel 604a and the LED(s) 605) is frictionally positioned in the tracheoscope channel 810 so as to resist movement within the channel 810.

Figure 9A:
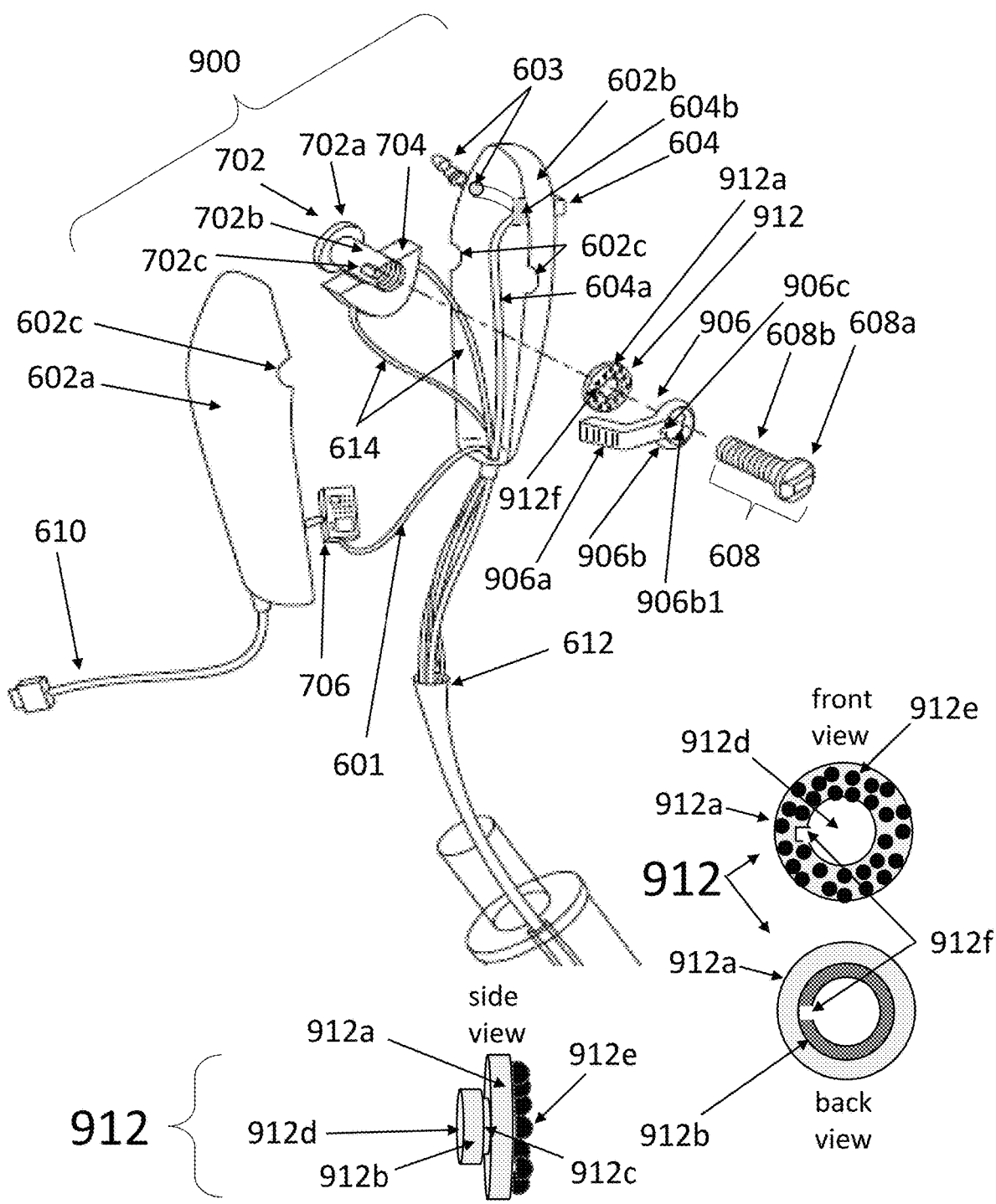
FIG. 9A illustrates an expanded view of a tracheoscope control device with an articulating tracheoscope according to another exemplary embodiment.

FIG. 9A illustrates an expanded view of a tracheoscope control device 900 with an articulating tracheoscope 601 according to another exemplary embodiment. The tracheoscope control device 900 is similar to the tracheoscope control device 600 as illustrated in FIGS. 6 and 7. However, in this exemplary embodiment a lever engagement unit 912 is disposed through an insertion hole 602c in the body 602 and provides a frictional resistance with respect to rotational movement of an articulation lever 906.

The lever engagement unit 912 can be formed of a rubber material and can include a front part 912a and a back part 912b separated from each other by an intermediate part 912c. However, the lever engagement unit 912 can be formed of alternative materials that provide the intended purposes as described herein, such as, for example providing a flexibility to be inserted through an insertion hole 602c and providing a predetermined amount of friction to resist rotational movement of the articulation lever 906a when engaged therewith.

The back part 912b and the front part 912a can both have a larger diameter than the diameter of the intermediate part 912c and the diameter of the insertion holes 602c of the body 602. At the same time the intermediate part 912c can have a diameter preferably the same size or slightly larger than the diameter of the insertion holes 602c and a width preferably the same size or slightly smaller than a width of a wall of the body 602. With this configuration the back part 912b of the lever engagement unit 912 can be pressingly fit through one insertion hole 602c of the body 602 such that the intermediate part 912c becomes fixed within one of the insertion holes 602c. Since the intermediate part 912c has a diameter the same size or slightly larger than the diameter of the insertion hole 602c and a width the same size or slightly less than the width of a wall of the body 602, the lever engagement unit 912 will not rotate with respect to the insertion hole 602c.

The lever engagement unit 912 can include a hole 912d extending through a middle thereof, to be described in more detail below. The lever engagement unit 912 can also include a plurality of bumps 912e extending from a side of the front part 912a opposite the side connected to the intermediate part 912c, and a key engagement groove 912e extending along the length of the hole 912d from the front part 912a to the back part 912b to receive a key type extension 702c therethrough so that the key type extension 702c can engage with the key engagement groove 912e.

The articulation lever 906 can include a first manipulation part 906a and a second part 906b. According to this exemplary embodiment, the second part 906b of the articulation lever 906 can include a plurality of bumps 906b1 on one side thereof which face the bumps 912e formed on the side of the lever engagement unit 912. These articulation lever bumps 906b1 can sit within spaces between the bumps 912d on the lever engagement unit 912 when the articulation lever 906 is brought into contact with the lever engagement unit 912. As a result of this configuration, when a friction screw 608 is tightened into threads in the tubular body 702b of the anchor 702, the bumps 906b1 on the lever 906 engage between and mesh with the bumps 912e on the front face of the lever engagement unit 912, thus preventing the lever 906 from rotating in either a clockwise or counterclockwise direction without a certain amount of force to overcome this friction.

The tubular body 702b of the anchor 702 can also include a key type extension 702c that engages with a key engagement groove 912f so that an articulation unit 704 that is integrally formed with the tubular body 702b will rotate only when the articulation lever 906 is rotated. Thus, the tracheoscope 601 and camera 601a will remain at a locked position until a predetermined amount of force is applied to the articulation lever 906 to overcome the frictional engagement.

Both the articulation lever 906 and the front part 912a of lever engagement unit 912 can have a plurality of bumps 906b1 and 912e respectively, such that the articulation lever 906 can move in very small increments as the adjacent opposing bumps are forced to slide over each other and then mesh with adjacent bumps. With this configuration small increments of rotational movement of the articulation lever 906 can be made, while the articulation lever 906 will stop moving and remain stationary when the force is no longer applied. This configuration provides the ability of a physician to move the camera 601a to any number of precise angles within an angular range of at least 180 degrees, and also provides the ability to lock the camera 601a in a desired position by simply releasing the articulation lever 906 or refraining from applying a sufficient amount of force required to overcome the frictional engagement.

It is to be noted that although the lever engagement unit 912 has been described as being formed of a rubber material, any type of flexible material can be used which will provide the configuration where bumps 912e thereon engage with bumps on the lever 606 such that when the articulation lever 606 is rotated by a predetermined amount of force the bumps 912e will flex enough to permit the bumps 912e to ride over the bumps 906b1 and then engage between a next set of bumps 906b1 on the lever 906. Accordingly, the tracheoscope 601 and camera 601a can be moved in incrementally small angles and locked at any desired angle without having to hold the lever 606 to keep the camera 601a stationary.

Although the lever engagement unit 912 has been described as having bumps 912a to prevent the articulation lever 606 from moving without a predetermined amount of force applied by an operator, the lever engagement unit 912 can alternatively be formed of any known alternative system that will prevent the articulation lever 606 from moving without a predetermined amount of force applied thereto. For example, the lever engagement unit 912 can be formed of a flexible rubber washer, which will apply an expanding force back on the articulation lever 606 once the frictional screw 608 is tightened to the point that the force of the articulation lever 606 on the rubber washer will prevent the lever 606 from moving on its own. Alternatively, the lever engagement unit 912 can include an aluminum washer with ripple waves along the circumference thereof while the circular engagement portion 906b of the articulation lever 606 includes similar ripple waves that correspond with the ripple waves of the lever engagement unit 912. Here the ripples on the articulation lever 606 will slide over adjacent ripples on engagement unit 912 each time a predetermined amount of force is applied to the articulation lever 606, thus effectively locking the articulation lever 606 in one position each time the articulation lever 606 is released.

Figure 9B:
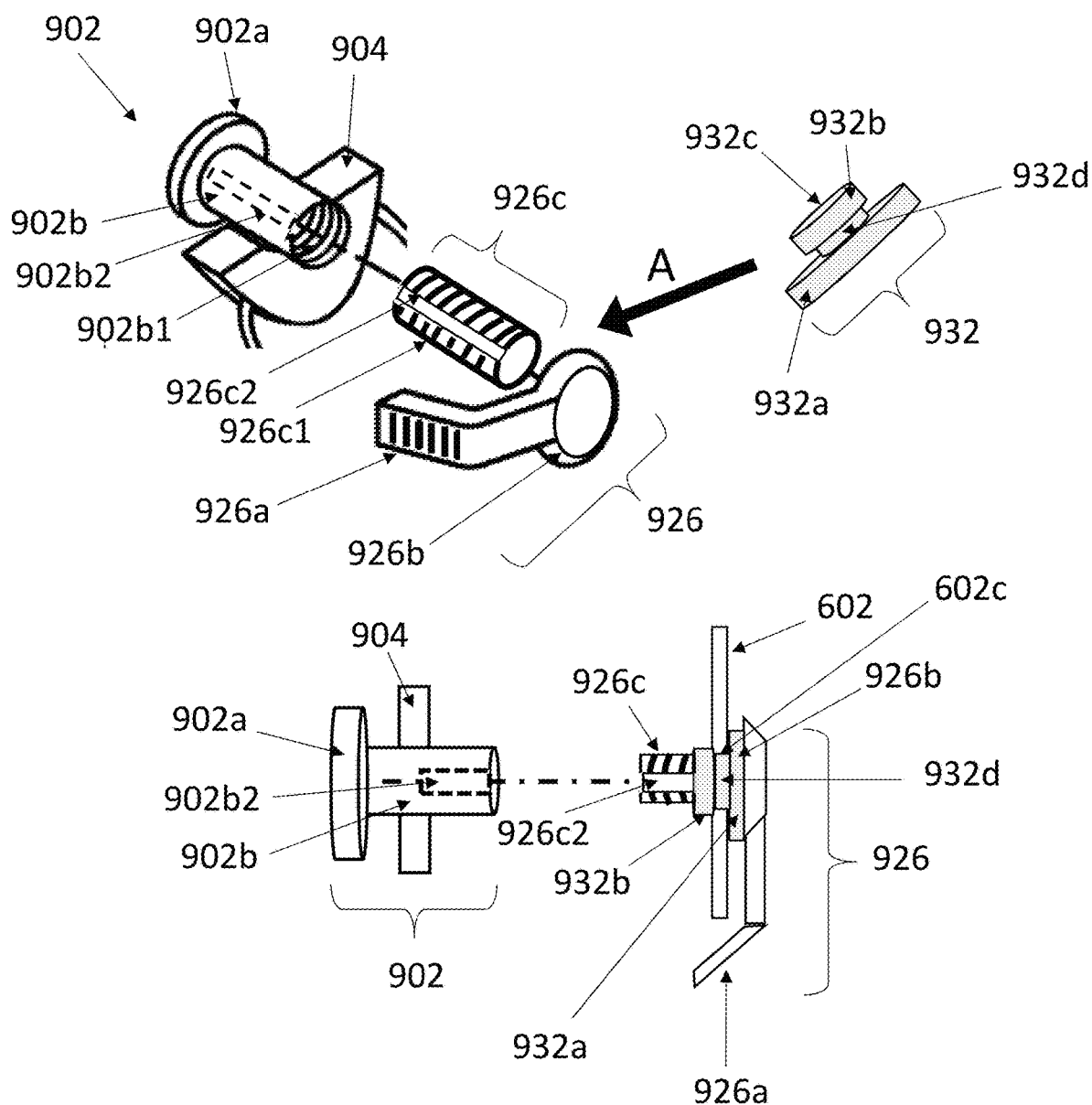
FIG. 9B illustrates an embodiment of an articulation lever and anchor configuration of a tracheoscope control device, according to another exemplary embodiment.

FIG. 9B illustrates an alternative embodiment of an articulation lever 926 and corresponding anchor 902 configuration. In this exemplary embodiment, the articulation lever 926 can be directly connected to the anchor 902 without the requirement of either a screw, a key type extension or a key engagement groove.

For example, the articulation lever 926 according to this exemplary embodiment can have a body portion 926a integrally formed with and extending from a circular engagement portion 926b. However, the circular engagement portion 926b according to this exemplary embodiment does not require a hole in which a screw can be inserted, but instead can include a tubular extension portion 926c extending therefrom and including a plurality of ribs 926c1 formed in parallel extending along a length thereof. The tubular extension portion 926c can also include a key engagement groove 926c2 extending across the ribs 926c1 along the length thereof to be engaged with a key type extension portion 902b2 formed along an interior of an anchor body portion 902b, as described in detail below. The circular engagement portion 926b.

Here the anchor 902 can include the tubular body portion 902b with a plurality of ribs 902b1 formed internally and in parallel. The tubular extension portion 926c of the articulation lever 926 can be inserted into the tubular body portion 902b of the anchor 902 such that the ribs 926c1 can be forced over the ribs 902b1 as the tubular extension portion 926c of the articulation lever 926 is pressed into the tubular body portion 902b. Also according to this exemplary embodiment a lever engagement unit 932, which is similar to the lever engagement unit 912, including a front part 932a and a back part 932b, can be provided. However, the lever engagement unit 932 does not require bumps. The back part 932b of the unit 912 is similarly press-fitted through an insertion hole 602c in the body 602 such that the lever engagement unit 932 is fixed in and does not move with respect to the insertion hole 602c since the front part 932a and the back part 932b are both larger than the insertion hole 602c, and an intermediate part 932d is tightly fit into the insertion hole 602c.

The circular engagement portion 926b of the articulation lever 926 does not require bumps since the lever engagement unit 912 does not have bumps. The tubular extension portion 926c of the articulation lever 926 can be inserted through a central hole 932c in the lever engagement unit 932 and then inserted into the tubular body portion 902b of the anchor 902. Here the internally formed key type extension 902b2 must be aligned with the external key engagement groove 926c2 formed along the tubular extension portion 926c of the lever 926. The engagement of the key type extension 902b2 with the external key engagement groove 926c2 ensures that the anchor 902, and hence the articulation member 904, will rotate only when the articulation lever 926 is rotated.

Once the tubular extension portion 926c of the lever 926 is inserted into the body portion 902b of the anchor 902 the articulation lever 926 and the anchor 902 can be pressed toward each other until the lever 926 is pressing the front part 932a of the lever engagement unit 932 against the body 602. Since the lever engagement unit 932 is pressed by the articulation lever 926, it will compress, causing an opposing force back on the lever 926. However, the ribs 926c of the articulation lever 926 will lock against the ribs 902b1 formed in the tubular body portion 902b of the anchor 902, thus keeping the articulation lever 926 in frictional engagement with the lever engagement unit 932. This frictional engagement between the articulation lever 926 and the lever engagement unit 932 will prevent the articulation lever 926 from rotating without a predetermined force applied thereto which will overcome the frictional engagement.

It is submitted that the articulation lever 606, 906, 926 according to the exemplary embodiments can be connected to the respective anchor 702, 902 in various alternative ways such that the anchor 702, 902, articulation member 704, 904 and the articulation lever 606, 906, 926 will rotate together, without departing from the principles and spirit of the present inventive concept as described herein.

Figure 10:
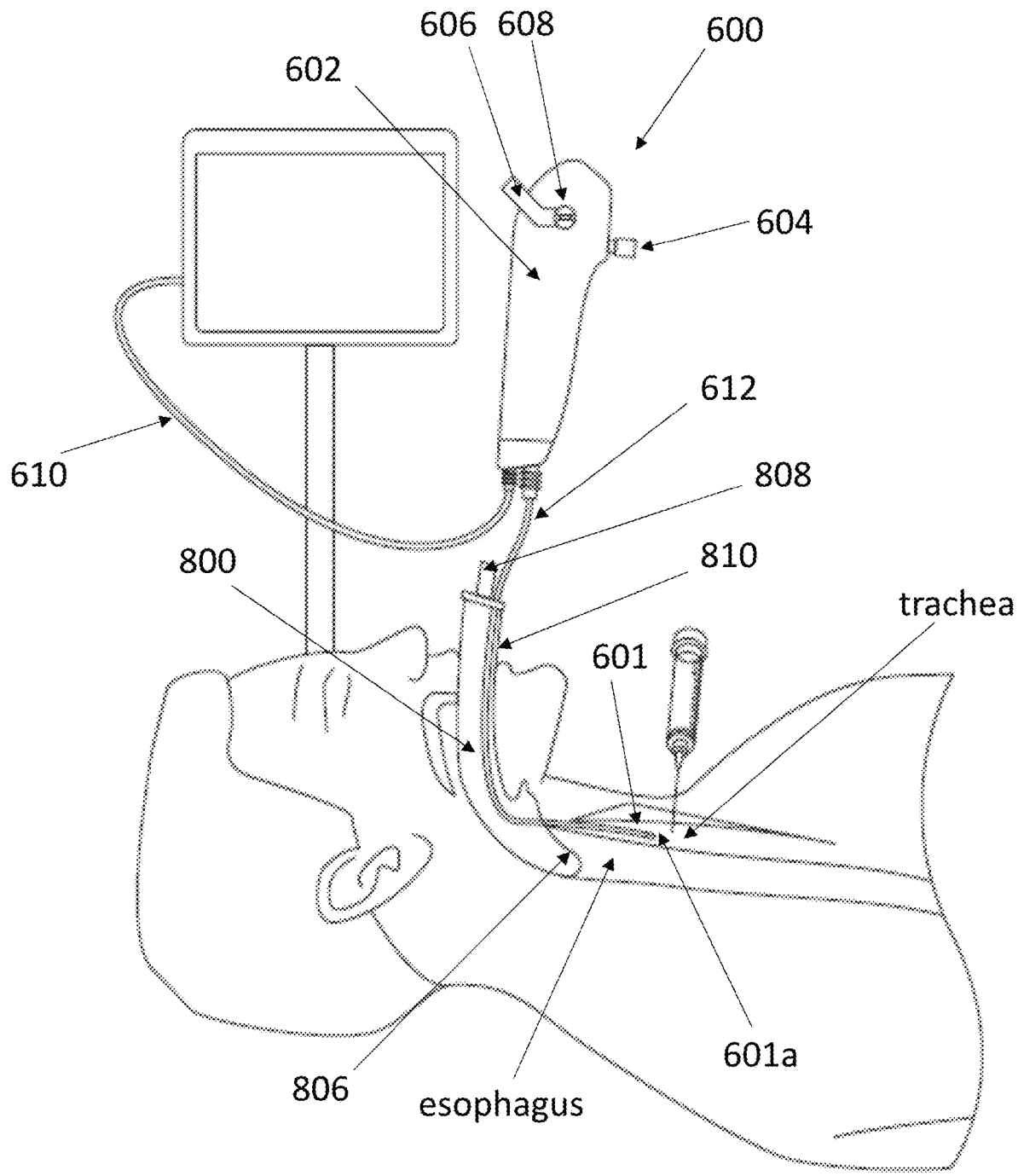
FIG. 10 illustrates an operational view of an articulating tracheoscope system including an articulating tracheoscope control device, a tracheoscope and a laryngeal mask airway (LMA) device combination, according to an exemplary embodiment of the present exemplary embodiment.

FIG. 10 illustrates an operational view of an articulating tracheoscope system 1000 that includes an articulating tracheoscope control device 600, a tracheoscope 601 and a laryngeal mask airway (LMA) device 800 combination, according to an exemplary embodiment of the present inventive concept. It is to be noted that the articulating tracheoscope control device 600, tracheoscope 601 and laryngeal mask airway (LMA) device 800 system is provided together as one disposable combination system, with the tracheoscope 601 friction fitted into the tracheoscope channel 810 of the LMA device 800. Also as illustrated, the tracheoscope 601 is friction fitted within the tracheoscope channel 810 such that the camera 601a rests facing the area where an incision for a tracheostomy is made when the LMA 800 is properly seated at a patient's esophagus. The physician can then move the lever 606 with precision to point the camera 601a at a desired location in the trachea of the patient.

With the articulating tracheoscope system as described in various exemplary embodiments above, only one physician is required to perform the entire process of a tracheostomy as a result of the following benefits thereof. First, the physician can use one hand to insert the LMA 800 into the patient's mouth and down to a patient's esophagus. The LMA 800, due its shape and diameter, will stop as the LMA cuff 806 becomes seated at the esophagus. The same physician can then manipulate the lever 606 on the an articulating tracheoscope control device 600 until a specifically desired area of the patient's trachea is in view on a monitor.

Since the lever 606 is configured to remain at a position in which the lever 606 is moved (i.e., after the physician is satisfied at the angle in which the tracheoscope 601 and camera 601a are facing by watching a monitor in which the video cable 610 is connected), the physician can place the articulating tracheoscope control device 600 down and free his/her hands to perform other procedures. For example, after the physician releases the articulating tracheoscope control device 600, the same physician can begin another required procedure of injecting an anesthesia into the patient's neck and trachea while monitoring how far into the trachea the need penetrates so that a success application or anesthesia is guaranteed. Then the physician can begin a tracheotomy procedure while continuing to monitor each step to ensure that the scalpel has made a successful incision. The physician can then use both hands to insert a trachea tube into the incision while monitoring the insertion of a trachea tube and monitor this process to ensure that the trachea tube extends properly down into the patient's trachea.

Although various embodiments of the present general inventive concept have been illustrated and described, it will be appreciated by those skilled in the art that changes may be made in these embodiments without departing from the principles and spirit of the general inventive concept, the scope of which is defined in the appended claims and their equivalents.

What is claimed is:

1. A tracheoscope control device, comprising:
an elongated hollow body including first and second axially aligned insertion holes extending through opposite sides thereof;
an articulation lever disposed at one side of the body and having a hole extending through one end thereof, the hole having a key-type groove formed therein;
an anchor having a head portion and a tubular body connected at one end to the head portion and having threads formed therein, the tubular body extending through the first axially aligned insertion hole, the anchor including:
a key type extension formed at an end of the tubular body opposite the end connected to the head portion to engage with the key type groove in the articulation lever, and
an articulation piece having a middle portion integrally formed with a middle portion of the tubular body;
a screw having threads formed along the body portion, the screw extending through the hole in the articulation lever, through the second axially aligned insertion hole and frictionally engaging with the threads in the tubular body of the anchor to engage the key type extension of the anchor with the key-type groove in the lever and create a frictional engagement between the lever and the elongated body; and
a tracheoscope including a first end disposed inside the hollow body and a second end disposed outside the hollow body and configured to capture external videos, the tracheoscope further including a pair of wires extending along opposite sides thereof, a first end of the wires being connected to opposite ends of the articulation piece and a second end of the wires being connected adjacent to the second end of the tracheoscope at opposite sides thereof.

2. The device of claim 1, further comprising:
a semiconductor chip disposed therein and including at least one processor to process video signals, the semiconductor chip being connected to the first end of the tracheoscope to receive the captures videos and to transmit processed video signals to an external display.

3. The device of claim 2, further comprising:
a camera disposed at the second end of the tracheoscope to capture videos.

4. The device of claim 3, further comprising:
a sheathing extending from the elongated hollow body to receive the tracheoscope and wires therethrough, the wires being configured to extend along opposite sides of the tracheoscope such that when the articulation lever is rotated the wires slide along opposite sides of the tracheoscope within the sheathing.

5. The device of claim 4, further comprising:
a suction channel including two sections, a first end of a first section extending from and air switch connected to a suction hole formed through the elongated hollow body, and a first end of a second section extending through the sheathing alongside the tracheoscope and terminating adjacent the second end of the tracheoscope; and
a suction button extending from the body at an angle substantially perpendicular to an axis extending through the pair of insertion holes, the suction button including:
a first button portion extending outside the body and being configured to be pushed inward, and
an air switch disposed inside the body and connected to a second end of the first section of the suction channel and to a second end of the second section of the suction channel such that when the button is pushed inward the air switch connects air flow between the first and second sections of the suction channel.

6. The device of claim 1, wherein the screw threads are formed of a flexible material that creates a friction with the anchor threads of the anchor such that the screw threads do not move with respect to the anchor threads until a sufficient amount of rotational force is applied to the screw to overcome the friction forme by the flexible material.

7. The device of claim 1, further comprising:
   a flexible lever engagement unit having a hole extending through a middle thereof and including:
      a back part press-fit against an insertion hole and disposed inside the hollow body, and
      a front part connected to the back part, the front part being press-fit against the insertion hole and disposed outside the hollow body, the front part causing a frictional resistance to rotational movement of the articulation lever with respect thereto.

8. The device of claim 1, wherein the flexible lever engagement unit further comprises:
   a plurality of bumps disposed along a surface of the front part, the bumps being configured to engage with bumps formed along a periphery of the hole in the articulation lever to mesh with the bumps on the articulation lever to provide a resisting force of rotation of the articulation lever with respect to the flexible lever engagement unit.

\* \* \* \* \*